United States Patent [19]
Swartz

[11] Patent Number: 5,289,821
[45] Date of Patent: Mar. 1, 1994

[54] METHOD OF ULTRASONIC DOPPLER MONITORING OF BLOOD FLOW IN A BLOOD VESSEL

[76] Inventor: William M. Swartz, 5030 Castleman St., Pittsburgh, Pa. 15232

[21] Appl. No.: 83,572

[22] Filed: Jun. 30, 1993

[51] Int. Cl.⁵ .............................................. A61B 8/12
[52] U.S. Cl. .............................. 128/661.09; 128/691; 128/662.03; 128/661.08; 128/662.06
[58] Field of Search ...................... 128/661.08, 661.09, 128/662.03, 662.06, 691

[56] References Cited

U.S. PATENT DOCUMENTS

| | | | |
|---|---|---|---|
| 4,602,624 | 7/1986 | Naples et al. | 128/784 |
| 4,628,942 | 12/1986 | Sweeney et al. | 128/784 |
| 4,649,936 | 3/1987 | Ungar et al. | 128/784 |
| 4,926,875 | 5/1990 | Rabinovitz et al. | 128/691 |
| 5,092,332 | 3/1992 | Lee et al. | 128/642 |
| 5,205,292 | 4/1993 | Czar et al. | 128/661.08 |

OTHER PUBLICATIONS

Pinnella, et al., "Direct Microvascular Monitoring with Implantable Ultrasonic Doppler Probes," *Journal of Microsurgery*, vol. 3, pp. 217-221 (1982).
May, Jr. et al., "Removable Thermocouple Probe Microvascular Patency Monitor: An Experimental and Clinical Study," *Plastic & Reconstructive Surgery*, vol. 72, No. 3, pp. 366-379 (1983).
Bandyk et al., "Detection of Technical Error During Arterial Surgery by Pulsed Doppler Spectral Analysis," *Archives of Surgery*, vol. 119, pp. 421-428 (1984).
Swartz, et al., "Direct Monitoring of Microvascular Anastomoses with the 20-MHz Ultrasonic Doppler Probe: An Experimental Study," *Plastic & Reconstructive Surgery*, pp. 149-158, Feb. (1988).

*Primary Examiner*—William E. Kamm
*Assistant Examiner*—George Manuel
*Attorney, Agent, or Firm*—Arnold B. Silverman

[57] ABSTRACT

A method of employing ultrasonic Doppler monitoring of blood flow in a patient's blood vessel includes, providing an ultrasonic transducer operatively associated with an ultrasonic processor by connection through an electrically conductive wire. The ultrasonic transducer-conducer wire assembly is secured to a strip of biologically inert or absorbable material, which is subsequently wrapped into contacting surrounding relationship with the exterior surface of the blood vessel and secured in such position to establish a cuff. The ultrasonic transducer-wire assembly is employed in a Doppler mode to monitor blood flow within the blood vessel. After completion of monitoring the ultrasonic transducer-wire assembly, but not the cuff are removed from the patient. The monitoring cuff is preferably positioned downstream, with respect to the direction of blood flow, of an anastomosis in the blood vessel.

17 Claims, 2 Drawing Sheets

METHOD OF ULTRASONIC DOPPLER MONITORING OF BLOOD FLOW IN A BLOOD VESSEL

BACKGROUND OF THE INVENTION

1. Field of Invention

The present invention relates to a method of monitoring blood flow in a blood vessel by employing ultrasonic Doppler technology and more specifically, it involves such a method which is advantageously employable in monitoring blood flow after microvascular surgery.

2. Description of the Prior Art

It has been known in connection with the monitoring of blood vessels after microvascular surgery to employ an ultrasonic Doppler probe which may take the form of a sleeve to which an ultrasonic transducer has been secured. After completion of monitoring, the probe and supporting sleeve must be surgically removed. See generally Swartz at al. "Direct Monitoring of Microvascular Anastomose with the 20-Mhz Ultrasonic Doppler Probe: An Experimental and Clinical Study," Plastic and Reconstructive Surgery, pages 149-158 (February 1988). See also Pinnella et al. "Direct Microvascular Monitoring with Implantable Ultrasonic Doppler Probes," Journal of Microsurgery, pages 217-221 (Summer 1982) and Bandyk et al. "Detection of Technical Error During Arterial Surgery by Pulsed Doppler Spectral Analysis," Arch. Surg. Volume 119, pages 421-428 (April 1984). It has also been known to employ implanted cuffs around nerves in order to stimulate nerve activity artificially or dampen nerve activity, or to deliver medication. See generally U.S. Pat. Nos. 4,602,624; 4,628,942; 4,649,936; and 5,092,332.

It is of great importance after microvascular surgery to monitor the region of the surgery in order to make sure that the blood flow is maintained at the desired level and that no problems, such as thromboses have occurred. Should thrombosis occur, the transferred tissue would die. Conventional techniques employ transcutaneous methods such as ultrasonic Doppler or laser Doppler. It has also been known to employ experimental sleeves which along with the wire and ultrasonic transducer must be surgically removed after completion of the monitoring period. Such monitoring is particularly important where the microvascular surgery has been performed on a blood vessel which is spaced below the skin surface.

It has been known to employ indirect means of monitoring the functioning of blood flow through blood vessels which have been subjected to microvascular surgery. For example, surface temperature measurements, transcutaneous PO$_2$ monitoring, photoplethysmography and laser Doppler flow meters have been employed. These approaches generally require an accessible exposed portion of the flap. Buried free tissue transfers and intraoral flaps cannot be monitored effectively by these methods.

It has also been known to employ an implantable thermocouple device which can be used without the need for exposed surface contact with the flap, but in general, this approach has been deemed inadequate and use has by and large has been discontinued. See generally, May et al. "Removable Thermocouple Probe Microvascular Patency Monitor: An Experimental and Clinical Study," Plast. Reconstr. Surg. 72:366 1983.

In spite of the foregoing known approaches there remains a substantial need for an improved means for monitoring blood flow within a patient.

SUMMARY OF THE INVENTION

The present invention has met the above described need. The present method of ultrasonic Doppler monitoring of blood flow in a patient's blood vessel includes employing ultrasonic processing means which are adapted to both provide pulsed energy to the transducer and receive returned signals from the transducer and process the same. The ultrasonic processing means are connected by an electrically conductive wire to an ultrasonic transducer. The wire and transducer assembly are preferably secured to a strip of biologically inert material, which strip is subsequently wrapped in intimate contact surrounding the exterior surface of the blood vessel in question to establish a cuff. The cuff is secured in the surrounding relationship and the transducer-wire assembly is employed in the Doppler mode to monitor blood flow within the blood vessel. After completion of the monitoring the ultrasonic transducer and wire are removed, but the cuff may remain in place.

The ultrasonic transducer and wire are preferably secured to the strip by introduction into the strip through a slit therein. Adhesive means may be employed to facilitate securement of the transducer in the desired position.

The method preferably positions the monitor downstream (with respect to the direction of blood flow) with respect to an anastomosis in the blood vessel.

The method may be employed in blood vessels which are disposed in spaced relationship below the skin.

An object of the present invention is to provide a reliable and efficient method of ultrasonic Doppler blood flow monitoring in a blood vessel which has been subjected to microvascular surgery.

It is another object of the present invention to provide such a method which eliminates the need for surgical removal of the cuff which secured the transducer and wire in the desired position.

It is a further object of the present invention to provide such a method which is usable both on arteries and veins.

It is a further object of the present invention to provide an efficient means for directly monitoring the arterial or venous anastomosis of free tissue transfers.

These, and other objects of the invention will be more fully understood from the following detailed description of the invention on reference to the illustrations appended hereto.

DESCRIPTION OF THE PREFERRED EMBODIMENTS

As used herein, the term "patient" will refer to members of the animal kingdom, including human beings.

Figure 1:
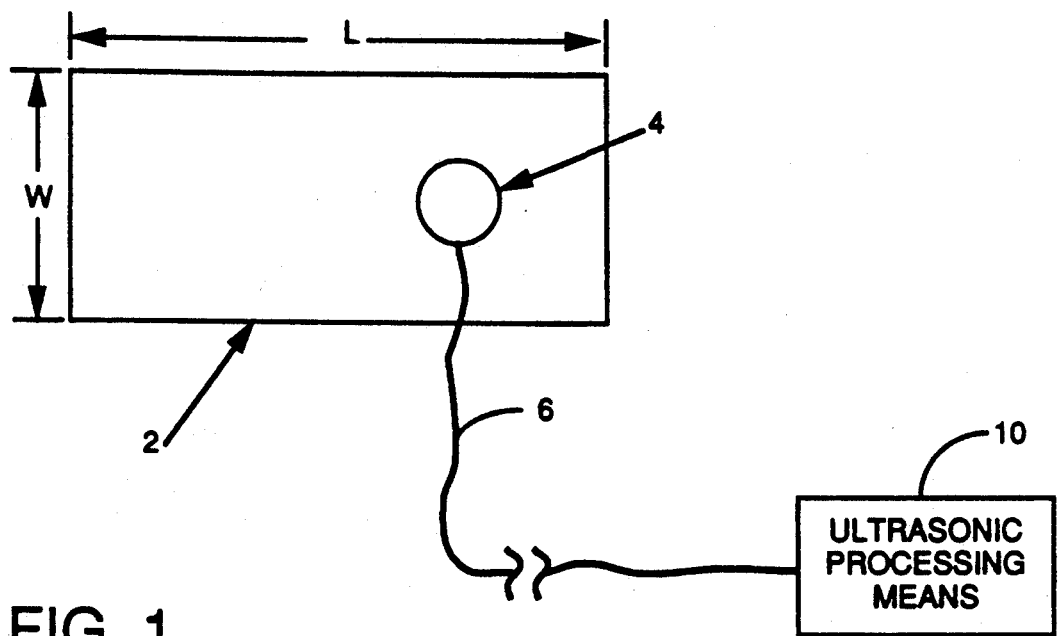
FIG. 1 is a schematic illustration of an initial phase of the method.

Referring in greater detail to FIG. 1, there is shown a strip 2 of biologically inert or absorbable material which has adequate strength to serve the intended purpose. A presently preferred material for this purpose is a polyfluorotetraethylene material such as that sold under trade designation Goretex which may have a thickness of about 0.026 to 0.030 inch. For the purposes of use within the present invention, the strip 2 may have a length L of about 6 to 8 mm and a width W of about 4 to 6 mm. All of these dimensions are presently preferred, but not limiting on the scope of the invention.

Secured to or within strip 2 in a manner to be described hereinafter is a transducer 4 which preferably is in the high frequency range of about 20 MHz and may be generally cylindrical, having a diameter of about 1.00 mm. A wire 6, which is preferably a silver wire which is silicone encased, connects the transducer with ultrasonic processing means 10 which serves both to energize the crystal 4 to emit an ultrasonic pulse and to receive the echo pulse and process the same. Those skilled in the art may readily determine the sort of signal processing/output and storage desired. It is presently preferred to use the audio signal in a qualitative fashion. A strip chart recording, oscilloscope presentation or computer data interface, for example, are alternative methods of storing and/or analyzing the signals.

Figure 2:
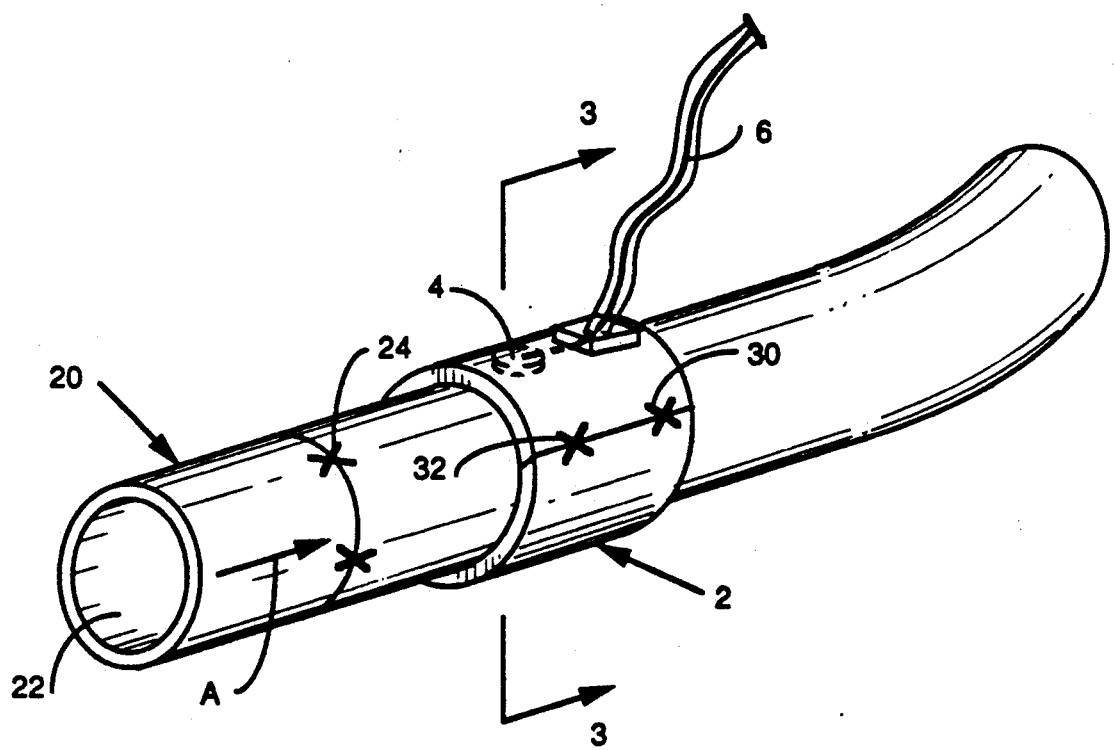
FIG. 2 illustrates the strip of the present invention positioned in surrounding relationship with respect to a blood vessel.

Referring to FIG. 2, there is shown a blood vessel 20 which may be a vein or artery which defines a lumen 22 through which blood will flow in the direction indicated by Arrow A. In the method of the present invention, the strip 2 is cut to desired length, such that, it will be capable of being positioned in the intimate surface to surface contact with exterior surface of blood vessel 20 in either a butt joint as shown in FIG. 2 or an overlapping joint, and secured in such position as by sutures 30, 32 with the strip 2 formed into the cuff-shape shown in FIG. 2. The transducer 4 is preferably oriented generally at an angle of about 45° F. to the exterior surface of the adjacent portion of blood vessel 20 and from this position can effectively provide information needed to determine blood flow through the vessel. It will be noted in the form shown that a cuff 2 has been positioned downstream with respect to the direction of blood flow from the anastomosis 24.

In this manner, an efficient means of monotoring a blood flow, post-surgically, to confirm that no thrombosis or other flow related potentially dangerous, undesired condition has occurred is facilitated.

Figure 3:
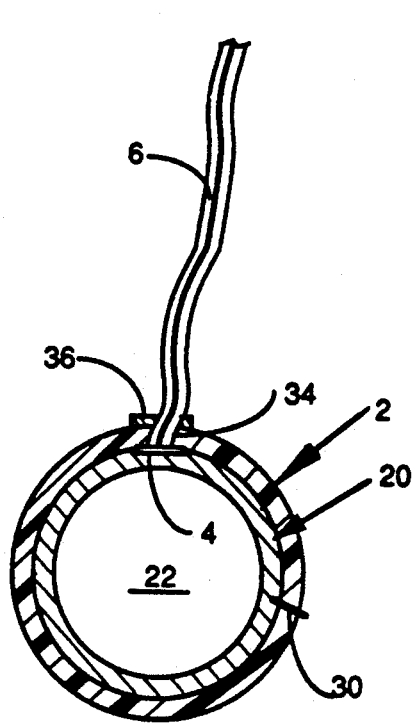
FIG. 3 illustrates a cross-sectional illustration of the blood vessel and cuff illustrated in FIG. 2, taken through 3—3 of FIG. 2.
Figure 4:
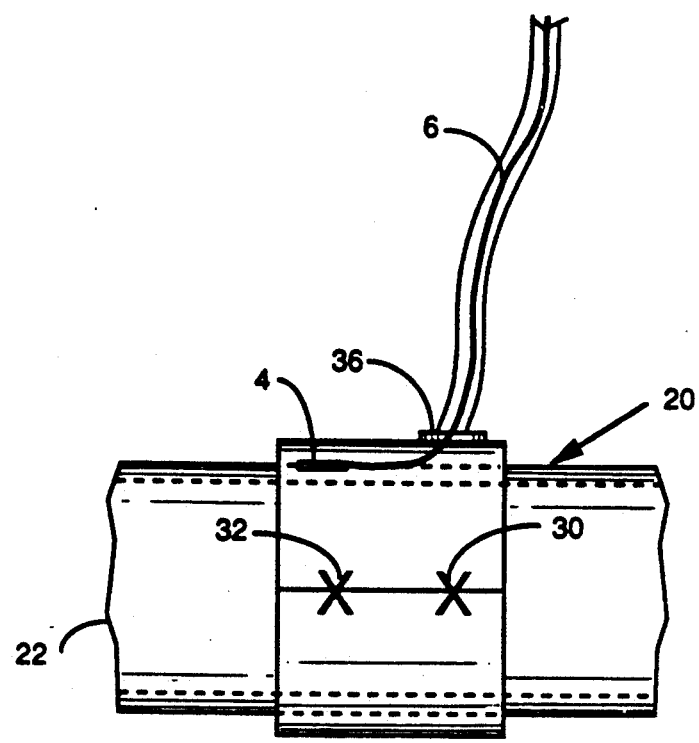
FIG. 4 is a fragmentary elevational illustration showing a portion of the cuff in position around the blood vessel.

Referring to FIGS. 3 and 4 in greater detail, it will be seen that a slit 34 has been made in the strip 2 to facilitate passage of transducer 4 into the interior of the strip 2. A suitable adhesive material, such as a room temperature vulcanizing silicone sealant 36 has been positioned adjacent slot 34 around wire 6, so as to secure wire 6 to the strip 2. In the alternative, a suture could be employed to effect such securement. In either event, the application of suitable tension to the wire 6 when it is desired to remove the wire 6-transducer 4 assembly should result in removal of these two elements as a unit.

In the embodiment shown in FIG. 3, the blood vessel 20 is shown in intimate surface-to-surface contact with the strip 2 which has been formed into a cuff. In some instances, there may be a space between the cuff 2 and the exterior of the blood vessel 2.

Figure 5:
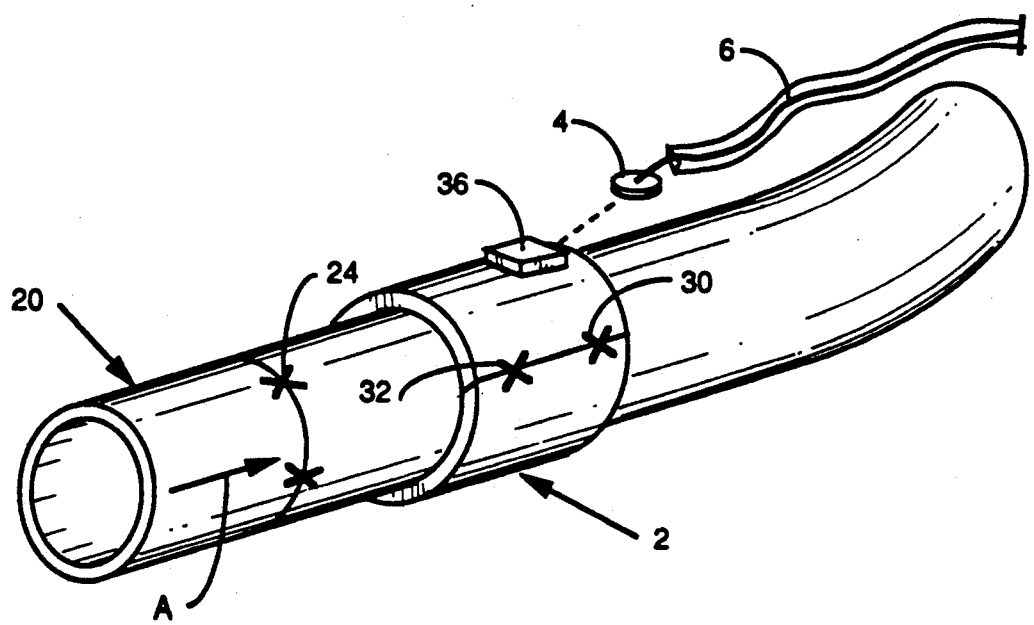
FIG. 5 is a schematic illustration showing an initial phase of transducer and wire removal from the cuff.

Referring to FIG. 5, in use after a period of about 3 to 7 days when it has been confirmed that the desired rate of blood flow is being maintained, the monitor is no longer needed. The wire 6, which penetrates the skin and extends to outside the body for connection to ultrasonic processing means 10 is disconnected from the cuff formed from strip 2 by means of a very small incision. The transducer 4, which is effectively secured to the wire 6 by any suitable means such as an adhesive or solder, for example, is removed with wire 6. By applying a pulling force to the wire 6, transducer 4 may be removed from the patient's body, leaving the cuff intact. It will be appreciated at this approach eliminates the need to reenter the general region of the prior surgery in order to remove a prior art type sleeve.

In the event that the monitoring process results in an indication that a predetermined level of flow restriction has occurred, it may be necessary or desirable to reenter the patient to perform exploratory surgery.

While the strip material 2, presently preferred is polyfluorotetraethylene, it will be appreciated that other biologically inert or absorbable materials having suitable strength may be employed in strip 2. Among the materials that may advantageously be employed are a material selected from the group consisting of silicone, absorbable polyglycoxilic acid (sold under the trade designation Dexon), and Dacron which is a trade designation for a straight chain polyester fiber derived from condensation of terephthalic acid with ethan-1, 2-diol.

The present invention may be employed to monitor blood flow within a vein or artery at a single location or a plurality of locations, depending upon the medical needs. One region of frequent use of microvascular surgery is in the patient's hand. In such case, where the surgery has occurred at a position spaced below the skin level, the wire 6 connecting the transducer 4 with the ultrasonic processing means 10 would extend out of the skin for purposes of this connection. As the number of days during which monitoring will occur, will be relatively short in the absence of unforeseen complications, the process is not particularly burdensome on the patient. It is generally preferred to employ the process at a particular location for about 3 to 7 days. The invention also provides the further advantage of eliminating surgery to remove a transducer supporting sleeve surrounding the blood vessel.

It will be appreciated that the method provides an effective means for monitoring blood flow within blood vessels of the patient after microvascular surgery while eliminating the need to surgically remove the entire monitoring device after the monitoring period is complete. All of this is accomplished in a manner which is surgically sound and does not in any manner interfere the effectiveness of the monitor.

As the ultrasonic processing means 10, wire 6, and the ultrasonic transducer 4, as well as their interaction and operation, are well known to those skilled in the art details of the same need not be provided herein.

Whereas, particular embodiments of the invention have been described herein, for purposes of illustration, it will be evident to those skilled in the art that numerous variations of the details may be made without departing from the invention as set forth in the appended claims.

I claim:

1. A method of ultrasonic Doppler monitoring of blood flow in a patient's blood vessel comprising providing an ultrasonic transducer operatively associated with ultrasonic processor means by an electrically conductive wire, securing the ultrasonic transducer to a strip of biologically inert or absorbable material, wrapping said strip in contacting surrounding relationship with the exterior surface of said blood vessel to establish a cuff, securing said cuff in said surrounding relationship, employing said ultrasonic transducer-wire assembly in a Doppler mode to monitor blood flow within said blood vessel, and after completion of said monitoring removing said ultrasonic transducer and said wire but not said cuff.

2. The method of claim 1 including employing said method to monitor blood flow in a blood vessel which has been subjected to microsurgery.

3. The method of claim 2 including employing said method in a blood vessel which is disposed at a position spaced beneath the surface of the skin.

4. The method of claim 3 including establishing said cuff at a position disposed downstream of an anastomosis with respect to the direction of blood flow in said blood vessel.

5. The method of claim 1 including removing said ultrasonic transducer and wire as a unit.

6. The method of claim 1 including employing a polyfluorotetraethylene material in said strip.

7. The method of claim 1 including securing said ultrasonic transducer within said strip by introducing it into said strip through a slit in said strip.

8. The method of claim 7 including securing the transducer-wire assembly to said strip by adhesive means.

9. The method of claim 8 including placing said adhesive means on said strip adjacent to said slit.

10. The method of claim 1 including determining if a thrombosis exists in said blood vessel.

11. The method of claim 10 including employing said method on a vein.

12. The method of claim 11 including employing said method on a blood vessel disposed within a patient's body.

13. The method of claim 12 including employing said method on a blood vessel disposed within a patient's hand.

14. The method of claim 10 including employing said method on an artery.

15. The method of claim 10 including performing exploratory surgery on said blood vessel if a predetermined level of reduced blood flow exists in said blood vessel.

16. The method of claim 1 including effecting removal of said ultrasonic transducer-wire assembly about 3 to 7 days after original insertion.

17. The method of claim 1 including positioning said strip in intimate substantially continuous contact with the exterior surface of said blood vessel, and securing said strip in position by sutures passing through a portion of said strip.

* * * * *